United States Patent [19]

Samson, Jr. et al.

[11] 3,954,414
[45] May 4, 1976

[54] SELF-CONTAINED APPARATUS FOR THE STORAGE PROCESSING OF BLOOD

[75] Inventors: Wilfred J. Samson, Jr., Hanover; Gerald D. Fox, Walpole; William E. Waye, Needham Heights, all of Mass.

[73] Assignee: Damon Corporation, Needham Heights, Mass.

[22] Filed: Mar. 29, 1974

[21] Appl. No.: 456,121

[52] U.S. Cl. .......................... 23/258.5 R; 312/294; 312/307; 312/313
[51] Int. Cl.² .................. A61M 1/03; A47B 47/00; A47B 49/00; A47B 88/00
[58] Field of Search ............ 23/258.5, 259, 258.5 R; 210/DIG. 23, 24, 83, 541; 312/294, 307, 313, 333, 334

[56] References Cited
UNITED STATES PATENTS

| | | | |
|---|---|---|---|
| 3,328,255 | 6/1967 | Ilg | 23/258.5 |
| 3,351,432 | 11/1967 | Van Dyck et al. | 23/258.5 |
| 3,399,040 | 8/1968 | Ilg | 23/258.5 |
| R27,132 | 6/1971 | Ilg | 23/258.5 |

Primary Examiner—Morris O. Wolk
Assistant Examiner—Michael S. Marcus
Attorney, Agent, or Firm—Kenway & Jenney

[57] ABSTRACT

Decanting apparatus for removing spent wash liquids from agglomerated red blood cells and like substances contained in an elongated pliable bag-like container has an inclined slide bed over which the container is draped. A cell-containing end portion of the container depends from the raised end of the slide bed, and the slide bed supports an elongated wash-receiving portion of the bag to maintain the bag under the tension required for decanting spent wash liquid from the former portion into the latter portion.

An elevator mechanism supports the raised end of the slide bed and enables an operator selectively to elevate the bed as required for the decanting operation.

A modular construction of the apparatus allows the slide bed and the elevator mechanism to be replaceably removed from the housing for cleansing and maintenance.

17 Claims, 6 Drawing Figures

3,954,414

SELF-CONTAINED APPARATUS FOR THE STORAGE PROCESSING OF BLOOD

BACKGROUND

This invention relates to apparatus for processing frozen blood in the course of reconstituting it fro infusion to a recipient. More particularly the invention provides improvements in apparatus for washing from red blood cells an additive introduced to preserve the cells during frozen storage.

Red blood cells frozen with a protective additive must be washed clean of the additive prior to resuspending the cells in plasma for subsequent infusion. The present invention effects the washing of the red blood cells within a closed, pliable, bag-like wash-container by means of a known technique that employs wash liquids having properties such that the cells when undisturbed tend to agglomerate and settle, rather than remain suspended in the liquid. This in turn makes it possible to decant the spent wash liquid from the agglomerated red cells. The result is that the spent wash liquid can be separated readily and quickly from the cells with minimal loss of cells and with maximal removal of spent liquid from the cells. U.S. Pat. No. 3,351,432, including the references cited therein, discloses this cell washing technique in further detail and discloses one apparatus for performing it.

The prior cell washing apparatus of that patent, however, has shortcomings which the instrument of this invention resolves. Specifically, the prior cell washing apparatus requires considerable vertical height to suspend the elongated wash container. For example, one device constructed according to the prior techniques for bench top insulation requires that a hole be cut through the bench top to provide vertical space in which to suspend the container.

The wash container has considerable length to provide a punch at one end for containing the red cells during the washing process, and to provide at the other end a bladder for receiving and containing successive applications of spent wash liquid. The container also has a medial section through which the wash liquid is transferred from the pouch portion to the bladder portion. Although the container in most instances does not have structure demarking such separate portions, it is convenient to consider the overall container structure as providing these portions for ease in explaining the invention.

The container typically is draped over a roller-like gate at the medial section with the cell-containing pouch depending on one side and the bladder depending on the other side. This known disposition of the container maintains the medial section under tension over the roller gate. This ensures that the gate provides the desired liquid barrier between the pouch and the bladder portions. The suspension of the container from the roller gate further ensures that the container is fully unfurled.

Prior art wash apparatus also is difficult to operate entirely by hand, and hence employs a motor drive to raise and lower the bag-suspending gate. This, however, has proven to result in relatively costly, cumbersome and noisy apparatus and does not readily allow facile manual control of the position of the gate.

Accordingly, it is an object of this invention to provide red blood cell washing apparatus having an improved mechanism for maintaining the wash container deployed under tension.

A further object is to provide red cell washing apparatus that requires significantly less vertical height than prior devices of this kind for deploying the wash container.

Another object is to provide red cell washing apparatus readily capable of direct manual operation.

Still another object of the invention is to provide apparatus of the above character that is relatively compact, that is relatively low cost to fabricate, and that provides ready access to the mechanisms thereof.

Other objects of the invention will in part be obvious and will in part be set forth hereinafter.

GENERAL DESCRIPTION

A red blood cell washing instrument embodying this invention provides support for the wash container in a small vertical space relative to the length of that container. The instrument supports the container draped over a vertically-movable gate to suspend the end, pouch portion that contains the red cells throughout the was operation. This end of the wash container is restrained from movement, so that movement of the gate lengthens or shortens the pouch portion and changes inversely the length of the container on the other side of the gate. When the gate is raised, the pouch portion of the container is elongated, so that it accommodates wash liquid, with which the cells are stirred. When the stirring is stopped, the red cells agglomerate and settle within the pouch. The gate is lowered to just above the agglomerated red cells, and then slowly raised. This decants wash liquid from the pouch through a medial portion of the container to a waste bladder, which the instrument deploys below the level of the gate.

After the first wash is decanted from the pouch, a second supply of wash liquid generally is delivered to the pouch, after which the stirring, agglomeration, settling and decanting operations are repeated. After decanting the final wash liquid from the red cell pouch, neutral saline can be admitted to the pouch for resuspending the red cells.

To provide the foregoing operation, the instrument of the present invention deploys the length of the container, which extends byond the gate away from the pouch, on a slide bed that is inclined downwardly from the gate. The slide bed supports this length of the container with a low coefficient of friction to allow the container freely to slide back and forth over the gate, as the latter member is raised and lowered. Moreover, as soon as a first supply of wash liquid is decanted into the bladder, the container becomes tensioned on the slide bed to pull against the gate sufficiently to make possible the removal of maximal volume of spent liquid from the agglomerated settled cells in the pouch with minimal loss of cells with the wash liquid. Further, the slide bed supports the medial and bladder portions of the container so that they fully unfurl readily.

A base support of the instrument rotatably mounts the lower end of the slide bed. Also mounted on the support is an elevator mechanism which carries the upper end of the slide bed with provision for raising and lowering it; the above-mentioned gate is at the uppermost end of the slide bed. A counterbalance mechanism is preferably provided to diminish the weight of the slide bed on the elevator mechanism. This enables an operator manually to raise and lower the slide bed selectively, as required for the washing and decanting operations, with little effort and hence with exacting control but minimal fatigue.

Further in accordance with the invention, the foregoing mechanisms are arranged as a modular unit. This unit is housed in a cabinet for ready removal and replacement as a single entity. This facilitates whatever maintenance, servicing or cleansing is desired for the instrument.

The invention accordingly comprises the features of construction, combinations of elements, and arrangement of parts exemplified in the construction hereinafter set forth, and the scope of the invention is indicated in the claims.

BRIEF DESCRIPTION OF DRAWINGS

For a fuller understanding of the nature and objects of the invention, reference should be made to the following detailed description taken in connection with the accompanying drawings, in which.

DESCRIPTION OF ILLUSTRATED EMBODIMENT

Figure 1:
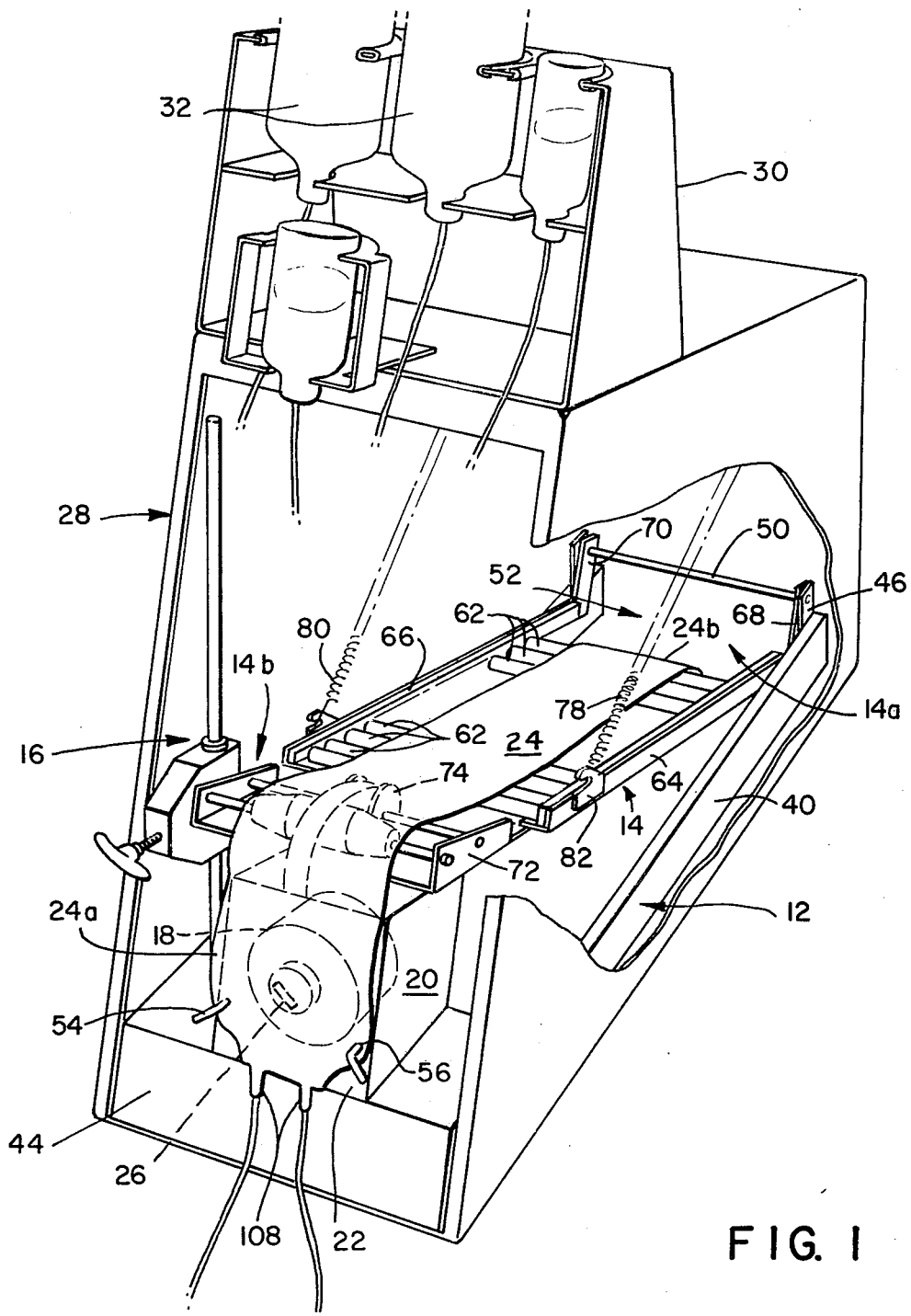
FIG. 1 is a perspective view, partly broken away, of a cell washing instrument emboding the invention and having a wash container operatively deployed thereon.

FIG. 1 shows a red blood cell washing instrument construced according to the invention with a base platform 12, an inclined slide bed 14, and an elevator mechanism 16 for the slide bed. The slide bed is pivotally mounted adjacent its lower, back end 14a to the platform, and the elevator mechanism 16 supports the upper, forward end 14b of the slide bed. Below the forward end of the slide bed a stir motor 18 is mounted within a motor housing 20 that has a front panel 22. The stir motor carries a permanent magnet on its shaft immediately behind the panel 22, which is of non-magnetic meterial. Motor rotation turns the magnet in a plane parallel to the panel 22. When a wash container 24 is in place as shown, this rotation of the motor magnet rotatably drives a magnetically-responsive stirrer 26 within the container to stir the container contents disposed in the pouch portion 24a in front of the panel 22.

With further reference to FIG. 1, the instrument has a cabinet 28 that closes the back, top, bottom and both sides. A rack 30 is mounted on top of the cabinet for supporting bottles 32 of the processing liquids with which the instrument is used. The cabinet 28 has an open front to provide access to the slide bed 14 and to the container being processed.

Figure 6:
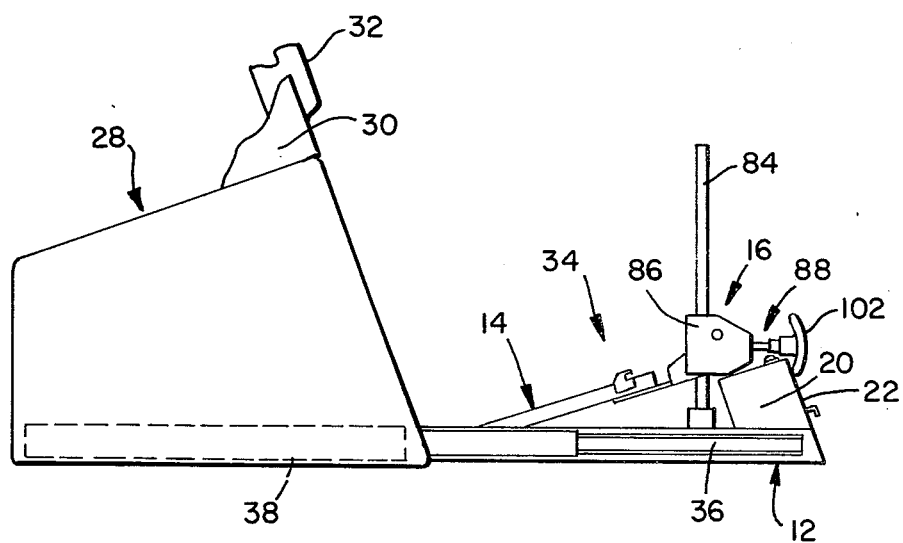
FIG. 6 is a side elevation view of the instrument of FIG. 1 with the modularly-arranged operative mechanism partially removed from the instrument cabinet.

The frontal opening of the cabinet 28 also allows the operative mechanism of the instrument to be installed into the cabinet. As shown in FIGS. 1 and 6, this mechanism, which includes the base platform 12, the slide bed 14, and the elevator mechanism 16, together with the stir motor in housing 20, is arranged in a single modular unit 34. Slide rails 36 affixed to both sides of the base platform 12 slidingly engage mating tracks 38 affixed to the inside of the cabinet sidewalls to support and mount the modular unit within the cabinet. With this modular arrangement and mounting, which can employ conventional rail-track units, the modular unit 34 can readily be partially removed from the cabinet, as shown in FIG. 6, or fully removed, for cleaning, repair or even replacement, and then re-installed or replaced, whichever is the case, with a minimum of effort and time. The cabinet 28 preferably includes whatever weights are required to prevent it from tipping forward when the modular unit 34 is slidably removed from it, as to the condition which FIG. 6 shows.

Figure 2:
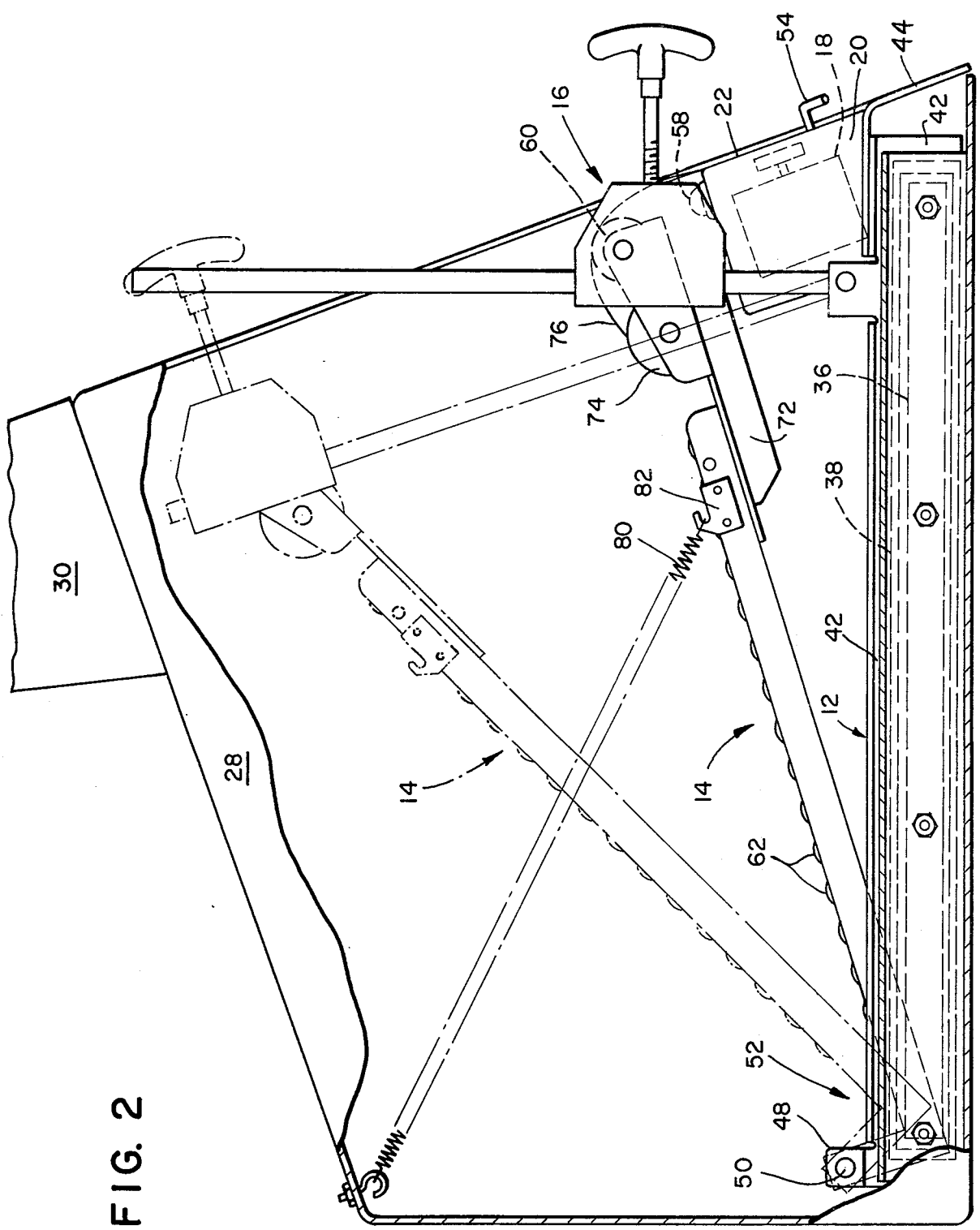
FIG. 2 is a side elevation view, partly broken away, of the instrument of FIG. 1.
Figure 3:
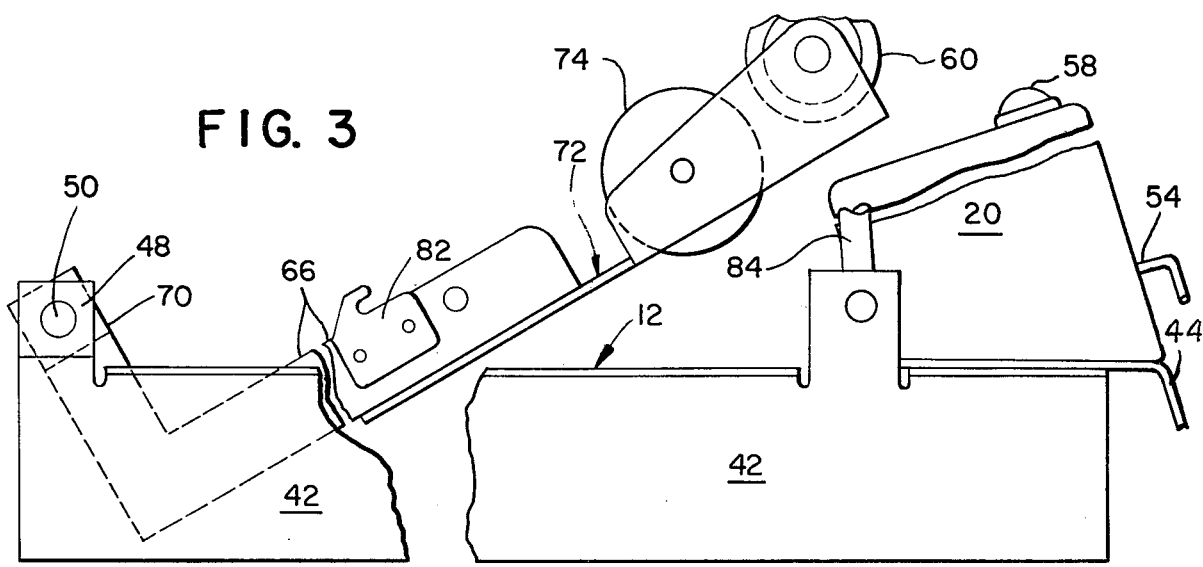
FIG. 3 is a fragmentary side elevation view of the base support and slide bed of the instrument of FIG. 1.

With reference to FIGS. 1, 2 and 3, the illustrated base platform 12 includes a rectangular platform frame with coextensive side members 40 and 42, to which the slide rails 36 are mounted, and a front cross member 44 on which the motor housing 20 is mounted. Each side member has at the back end an upstanding post 46, 48. A shaft 50 interconnects these posts as part of the platform frame and mounts the slide bed 14 to the platform 12, adjacent the top of these posts, for rotation of the bed about the axis of the shaft. This construction locates the axis of bed rotation above the lower end of the bed, for the purpose of providing a space 52 through which the end of the container 24 distal to the pouch 24a can depend, as FIG. 1 shows, when the bed is in a lowered position.

The base platform 12 further includes holding means for releasable attachment to the pouch end 24a of the wash container. The illustrated instrument provides these holding means as a pair of hooks 54 mounted on the panel 22 and which secure the pouch end 24a at a selected level on the instrument. An operator slips sealed passages 56, which extend through the container 24, over the hooks to fixedly position the container with the pouch 24a in front of the panel 22. The hooks also anchor this container end against movement due to the sliding pull of the rest of the container down the slide bed 14. This results in the bag passing over the frontal edge of the slide bed under tension, as is desired.

The stir motor within the housing 20, and lamps 58 on the top of the housing, are provided in the same manner as in prior constructions of this instrument, such as is described in the above-noted U.S. Pat. No. 3,351,432.

The slide bed 14 provides a self-tensioning yet contained support for the length of the container 24 which extends beyond a container-suspending roller 60, which is carried at the frontal end of the bed and provides the previously-mentioned gate. The bed supports the bag-like container in a manner such that the container is in a stable state when fully unfurled, as shown in FIG. 1, so that it unfurls with minimal operator attention after being anchored on the hooks 54 and arrayed on the bed 14. Further, the slide bed supports the container in a manner such that the weight of the container length beyond the roller 60, and the liquid contained therein, exert on the container pouch 24a an upward pull, which the hooks 54 resist. The result is that the bag passes over the roller 60 under tension.

This tension in the container has been found desirable to maximize the separation of wash liquids from the red cells and to minimize the loss of red cells from the pouch 24a. A sharper interface develops between the settled red cells and the liquid in a taught container than in a flacid one. Moreover, the flow of liquid over the roller from the pouch can be controlled more carefully, to avoid carrying over red cells, when the container is taught.

Figure 4:
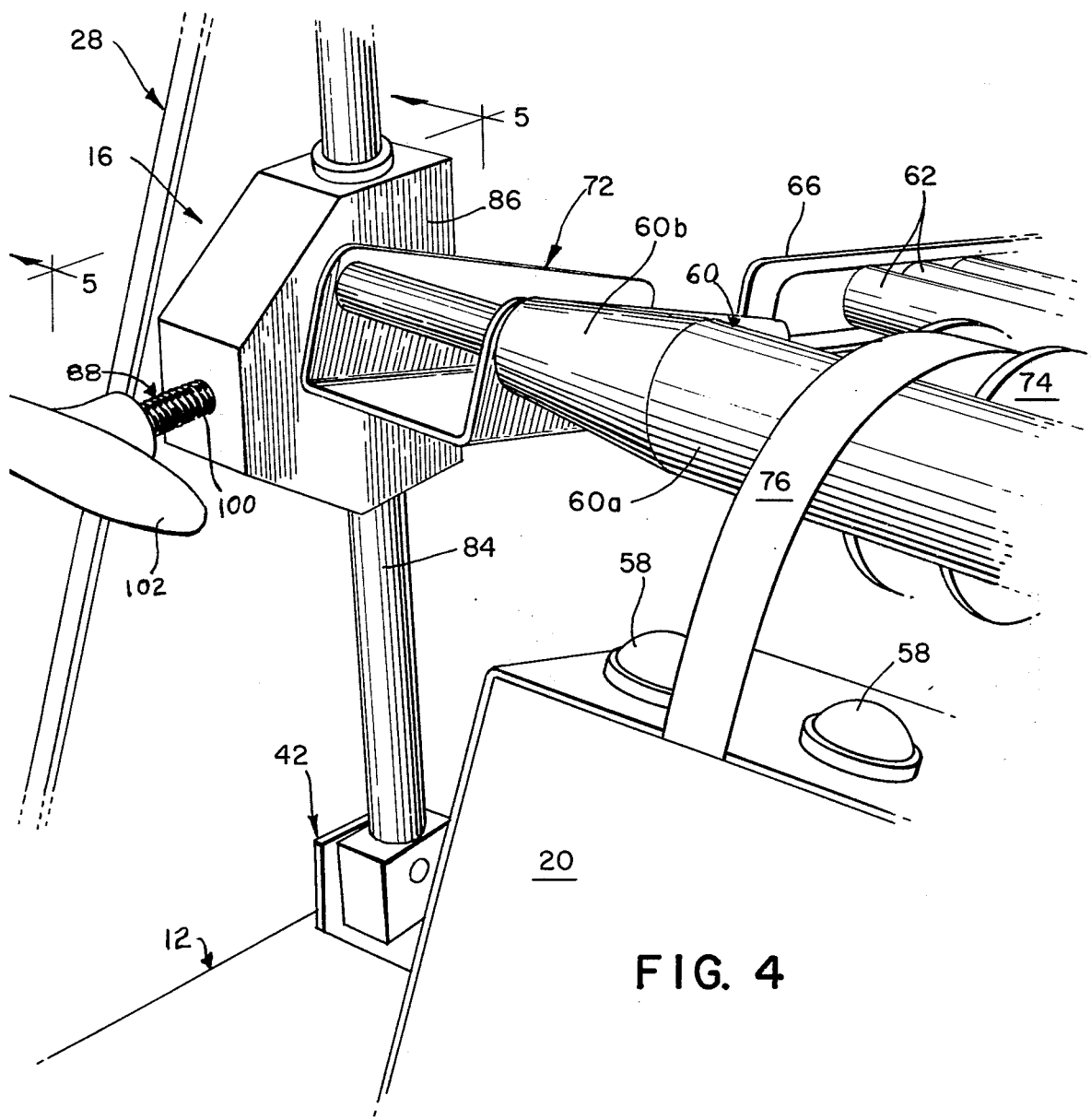
FIG. 4 is a perspective fragmentary view of the elevator mechanism of the instrument of FIG. 1.

Further, the illustrated front roller 60 has, as FIG. 4 shows, a cylindrical center section 60a and narrowingly tapered end sections 60b in order to restrict the flow of small volumes of liquid over the roller. This restricted flow aids the operator in attaining a finer control in exuding small volumes of spent wash solution.

Referring to FIGS. 1 and 2, the illustrated slide bed is constructed essentially as a roller conveyer, with a linearl succession of side-by-side rollers 62 journaled at each end between a pair of side supports 64, 66. The back, lower end 14a of the slide bed is rotatably joined to the base support 12, by way of the shaft 50, with arms 68, 70 extending upward from the side supports 64, 66 respectively, and through which the shaft passes. The slide bed has rollers 62 along the major part of the slide bed length, but preferably not along the full extent. As FIG. 1 indicates, the side supports 64, 66 extend at the lower end 14a beyond the rollers 62 for a length equivalent to the order of two or three roller diameters. This roller void forms part of the space 52 into which the container end 24b can drop, to further increase the tension over the front roller 60.

At the upper, forward end 14b of the slide bed, a roller bracket 72 extends forward from the side supports and the rollers. The forward roller 60 is journaled to this bracket, as FIG. 4 details. In addition, a spring-mounting roller 74 is journaled to the bracket intermediate the front roller 60 and the first of the slide rollers 62. The slide rollers 62, the front roller 60, and the spring roller 74 all have rotation axes which are parallel to the shaft 50 about which the slide bed is rotatable. Further, these rotation axes of the slide bed roll elements are arrayed as FIG. 2 shows with the axis of the frontal roller 60 spaced slightly above the plane in which the slide bed rollers are centered, and with the spring roller rotation axis at an intermediate level.

The spring roller 74, shown in FIG. 4, forms a reel for an extensible support 76 for the portion of a container 24 between the motor housing panel 22 and the slide bed. This illustrated support 76 is a metal, coil spring, band that selfwinds on the roller 74, preferably with a constant spring force. The spring support band is fixed at one end to the motor housing 20, is trained over the roller 60, and recoils in a central recess on roller 74 between circumferential flanges.

As FIGS. 1 and 2 show, a counter-weight mechanism, illustratively provided by coil springs 78, 80, at least in part unweights the slide bed from downward (clockwise in FIG. 2) rotation about the shaft 50. This facilitates operator positioning of the slide bed by greatly diminishing the force required to raise the bed. The coil springs 78 and 80 are tensioned between the upper back corner of the instrument cabinet 28 and the forward portion of the slide bed. In particular, the illustrated construction employs spring hooks 82 attached to each slide bed support 64, 66. The arrangement of the springs is such that they are increasingly tensioned as the slide bed is lowered from its uppermost position, so that the restoring force of the springs on the slide bed tends to offset the moment of clockwise rotation of the slide bed. The hook attachment of the springs to the slide bed enables them readily to be disengaged from the slide bed for removing the modular unit 34 from the cabinet 28, as discussed above, and conversely for reattaching the springs to the slide bed after reassembly of the modular unit within the cabinet.

Figure 5:
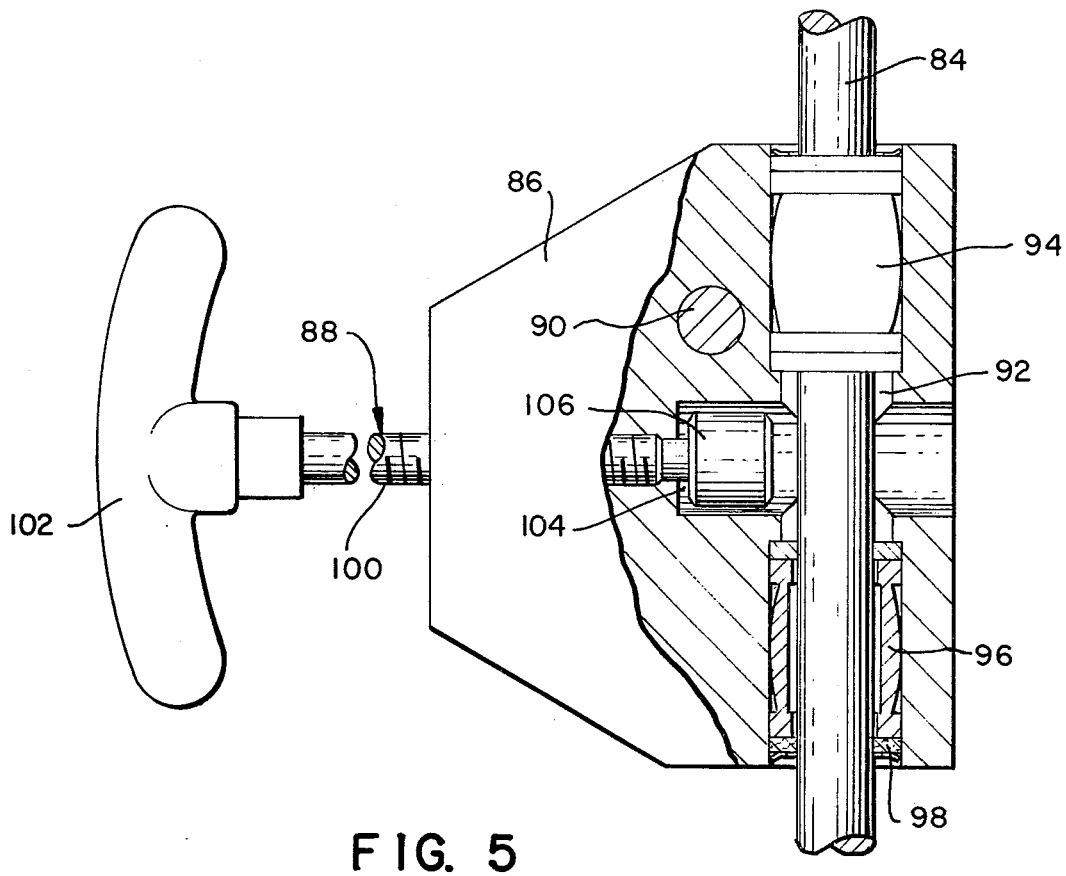
FIG. 5 is a sectional side elevation view, taken along section line 5—5 of FIG. 1 and partly broken away.

Turning to FIGS. 4 and 5, the illustrated elevator mechanism 16 includes an upstanding elevator rod 84 mounted at its base end to the base platform 12 for rotation about an axis parallel to the shaft 50 (FIG. 1). A clamp block 86 is slidably seated on the rod and fitted with a clamp 88 to fix the block at any height along the rod 84. The clamp block also supportingly carries the forward end of the slide bed 14 by means of a trunnion extension 90 on the frontal roller 60 journaled in the block.

More particularly, the front roller trunnion extension provides a rotatable and cantilevered support of the slide bed from the clamp block 86. The clamp block 86 further has a through bore 92 (FIG. 5) within which the rod 84 passes. The bore is fitted with a pair of vertically-spaced linear ball bearings 94, 96 which seatingly engage the rod. Sliding seals 98 exclude dirt and liquid contaminants from entering the bearings.

The illustrated manually-adjustable clamp 88 includes a threaded shaft 100 fitted with a handle 102 at one end and threaded into the block 86 at right angles to the bore 90 along a passage 104 centered on and coplanar with the bore 92, i.e. in the plane of FIG. 5, at the mid-point in the bore. In an enlarged section of passage 104 adjacent the bore 92, the shaft 100 carries an enlarged pressure plug 106, affixed to its inner end. When the shaft 100 of clamp 88 is threaded to withdraw the plug from the rod 84, the clamp block 86 freely slides up and down along the elevator rod. In this condition, as shown in FIG. 5, the slide bed can be raised and lowered essentially at will, by operator manual control exerted at handle 102. To clamp or fix the slide bed at a selected inclination or elevation, the operator simply turns the handle 102 to thread the shaft into the clamp block and thereby engage the pressure plug against the elevator rod 84. Typically less than a quarter turn is required to change the clamp between a tightly fixed condition and a condition where the pressure plug is totally free of the elevator rod 84.

With this construction, the single clamp block and a single elevator rod can securely and firmly support the slide bed, and allow ready control of its position.

The operation of the illustrated instrument typically commences with the installation on it, as shown in FIG. 1, of an empty container 24. The installation simply involves hooking the pouch end onto the hooks 54, 54 and draping the container in front of the motor housing panel 22, over the front roller 60 and down along the slide bed 14. A vacuum line preferably is connected to one of the two ports 108 leading from the container to evacuate any air or other gas in it. With the slide bed raised, red cells to be glycerolized are delivered to the container pouch 24a, followed by the introduction, with the stir motor on, of a glycerol solution with which the cells are to be preserved by freezing.

When the preserved, glycerolized cells are to be used, they are thawed in the container 24, and it is then installed on the instrument. The slide bed typically is down at this time; it is then raised to a position as shown in phantom in FIG. 2. Thereafter, a first wash liquid is introduced to the container pouch via a port 108, typically by gravity flow from the rack 30. The slide bed should be elevated sufficiently so that the front roller 60 is well above the upper level of liquid in the pouch. The stir motor 18 is then energized to mix the red cells with the wash liquid, after which the red cells are allowed to agglomerate and settle (with the stir motor off).

Next, the spent liquid is decanted from the pouch by lowering the slide bed to bring the front roller 60 to a level just above the level of the settled red cells. The descent preferably is gradual and controlled to avoid resuspending the red cells. Due to the downward incline of the slide bed, the spent liquid flows by gravity into the container bladder, filling end 24*b*. This increases the tensile pull of the container over the front roller 60, which is desired. The slide bed may be raised and again lowered to decant off a further quantity of spent liquid, before further processing. When the slide bed is raised, the end section 24*b* of the container may be drawn out of the space 52. However, when the bed is again lowered, the end of the container will again drop behind the lowermost roller, where it exerts increased tension for the actual decanting operation.

The wash operation typically proceeds with the introduction of further wash liquid, followed by stirring, agglomeration and settlement of the red cells, and decanting the spent liquid from the container pouch into the container bladder. All the manipulation of the slide bed for these operations is readily affected by the operator with one hand on the handle 102. With the control this handle affords, the operator can carefully, selectively raise or lower the slide bed, as well as lock the bed in whatever position is desired and, alternatively, release it.

When the desired washing and decanting operations are complete, the washed red cells typically are suspended in reconstituting fluid, again admitted to the pouch by way of a port 108. After the cells are mixed with the reconstituting fluid by means of the stir motor, the resuspended cells are drained from the container into a separate bag, for storage until subsequent infusion or other use. The container 24 is readily removed from the instrument, with the total volume of all spent liquids, and the machine is ready for washing a further batch of red cells within a fresh container.

By way illustrative example, an instrument constructed in the foregoing manner employs a slide bed rotatable between a minimum inclination of 18° above the normally horizontal base platform 12 and a maximum inclination in the order of 45°. A low inclination is desirable to reduce the vertical height of the instrument. However, the lower inclination must be large enough so that the container will slide down the slide bed, overcoming static and sliding friction, after a small volume of spent liquid is decanted into it. Thus the materials and construction selected for the container and for the slide bed will impact the minimal inclination. The foregoing value of 18° is for a container of synthetic resin (plastic) and a slide bed with bearing-journaled rollers. Angles as low as 15° may be found usable, depending on the structures and materials; also a fixed weight added to the lowermost end of the container will aid operation with shallow angles.

It will thus be seen that the objects set forth above, among those made apparent from the preceding description, are efficiently attained. Since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described the invention, what is claimed as new and secured by Letters Patent is:

1. In apparatus for decanting liquid from a first end portion to a second end portion of an elongated, pliable, bag-like container, said apparatus having support means and having holding means for releasable attachment to such container for affixing the first end portion thereof to the support means, the improvement comprising
   A. inclined, container-supporting slide means,
      1. elongated between upper and lower ends thereof and disposed with the elongation thereof between said ends aligned with said holding means such that the container attached to said holding means extends along said slide means in the direction from said upper end to said lower end,
      2. mounted on said support means with said upper end disposed above said holding means and above said lower end, and
      3. selectively rotatable relative to said support means to change the inclination thereof between said ends, thereby to change the elevation of said upper end relative to said holding means and to said lower end, and
   B. positioning means connected between said slide means and said support means for selectively positioning the relative elevation of said upper end of said slide means.

2. In an instrument for the washing of red blood cells contained in a pliable bag-like container elongated between first and second ends, and having means forming a base support with two opposed ends and fitted with holding means adjacent one end thereof for attachment to such a container for disposing the first end thereof at a selected level relative to said base support, the improvement comprising
   A. slide means having first and second slide ends and a slide bed therebetween, said slide means being pivotally mounted adjacent said second slide end to said base support means adjacent the other end thereof for elevational rotation of said first slide end relative to said second slide end above a lower position where said first slide end is at a selected level relative to said holding means and is above said second slide end, said slide bed and said slide ends being aligned with said holding means whereby a container attached to said holding means passes over said first slide end to said slide bed, and
   B. means coupled between said slide means and said base support for selectively positioning the elevation of said slide means first end relative to said holding means.

3. In an instrument according to claim 2, the further improvement wherein said positioning means comprises
   A. an elevator rod connected at one end to said base support for rotation relative thereto about an axis parallel to the rotation axis of said slide means, and supportingly connected to said slide means adjacent said first slide end with said slide means free to slide therealong, and
   B. brake means for selectively holding, and alternatively releasing, the sliding position of said slide means along said elevator rod.

4. In an instrument according to claim 2, the further improvement
   A. in which said slide means is elevationally movable between said lower position and a raised position, and
   B. further comprising counterbalance means operatively connected between said slide means and said base support means and at least in part counterbalancing gravitational rotation of said slide means to said lower position.

5. In an instrument as defined in claim 2, the further improvement
   in which said slide means comprises a roller conveyer-type slide bed extending at least part way between said first and second slide ends.

6. In an instrument as defined in claim 2 the further improvement in which said slide means has a support surface which presents a low coefficient of friction to an article resting thereon thereby to slide the article in the direction of said second slide end.

7. In an instrument as defined in claim 2, the further improvement
   A. wherein said slide means and said positioning means form with said base support a single modular unit,
   B. comprising an instrument cabinet for housing said modular unit, and
   C. comprising replaceably separable rail and track means being connected one to said modular unit and one to said housing, for removably and replaceably mounting said modular unit within said cabinet.

8. Apparatus for decanting liquid from a first end portion to a second end portion of an elongated, pliable, bag-like container, said apparatus having support means with opposed ends and which carries container-holding means adjacent one end thereof for releasable attachment to such a container for affixing the first end portion thereof to said support means at a selected level, and further comprising
   inclined slide means
   1. having upper and lower ends and elongated therebetween to provide a container-supporting, platform-like slide bed,
   2. disposed with said slide bed aligned, along the direction of the spacing between said upper and lower ends, with said holding means, and further disposed with said upper end located above said lower end and above said selected level, and
   3. having said lower end rotatably mounted on said support means adjacent the other end thereof for selective rotation of said slide means relative to said support means to change the inclination of said slide bed and thereby change the relative elevation of said upper end above said selected level and said lower end.

9. Decanting apparatus as defined in claim 8 in which
   A. said slide means upper end comprises a frontal roller for supportingly suspending such a container trained thereover between said holding means and said slide bed, and
   B said slide bed comprises a bed of parallel rollers, said frontal roller and said bed rollers being rotatable about axes parallel to the axis of rotation of said slide means.

10. Decanting apparatus as defined in claim 8
    further comprising counterweight means connected with said slide means for unweighting said upper end from unrestricted gravitational rotation relative to said support means and about said lower end.

11. Decanting apparatus as defined in claim 8 further including means for disposing said lower end of said slide bed at an elevation below said selected level at which said holding means disposes the first end of such a container.

12. Decanting apparatus as defined in claim 8 further comprising positioning means including
    A. vertically extending guide means connected with said support means and with said slide means, and
    B. manually-operable clamp-and-release means selectively engageable with said guide means for holding the elevation of said slide means upper end fixed relative to said guide means and said support means, and, alternatively, for releasing said upper end for rotational movement of said slide means.

13. Decanting apparatus as defined in claim 8 further including
    means connected between said slide means and said support means for selectively positioning the elevation of said upper end of said slide means.

14. Decanting apparatus as defined in claim 8 in which said slide means includes a container-suspending slide gate forming said upper end thereof.

15. Decanting apparatus as defined in claim 8 in which said support means has a normally horizontal base and in which said slide means is rotatable between a minimum incline where said upper end is proximal to said selected level provided by said holding means and a further incline where said upper end is more distal from said selected level, and further characterized in that said minimum incline is not less than fifteen degrees relative to the horizontal base of said support means.

16. Decanting apparatus as defined in claim 8 in which said slide bed includes means for imparting, to a weighted length of such container disposed thereon, a downward slide therealong for all inclinations of said slide means between a minimum incline where said upper end is relatively closely above said holding means and a maximum incline where said upper end is further removed above said holding means.

17. Decanting apparatus as defined in claim 16 further characterized in that said slide means includes means forming a container-accommodating space through said support means adjacent said lower end thereof for suspending the second end of such container from said lower end.

* * * * *

UNITED STATES PATENT AND TRADEMARK OFFICE
CERTIFICATE OF CORRECTION

PATENT NO. : 3,954,414
DATED : May 4, 1976
INVENTOR(S) : Wilfred J. Samson, Jr., Gerald D. Fox, William E. Waye It is certified that error appears in the above-identified patent and that said Letters Patent are hereby corrected as shown below:

Column 1, line 7, change "fro" to --for--.

Column 1, line 40, change "punch" to --pouch--.

Column 2, line 23, change "was" to --wash--.

Column 2, line 46, change "byond" to --beyond--.

Column 3, line 38, change "construced" to --constructed--.

Column 3, line 48, change "meterial" to --material--.

Column 4, line 67, change "taught" to --taut--.

Column 5, line 3, change "taught" to --taut--.

Column 5, line 12, change "linearl" to --lineal--.

Column 7, line 41, after "way" insert --of--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*